US012350408B2

(12) United States Patent
Beers et al.

(10) Patent No.: US 12,350,408 B2
(45) Date of Patent: Jul. 8, 2025

(54) COAXIAL TUBULAR FLUID TREATMENT DEVICE AND SYSTEM

(71) Applicant: ICA TriNova, LLC, Newnan, GA (US)

(72) Inventors: Steven Beers, Newnan, GA (US); Joel Tenney, Marietta, GA (US)

(73) Assignee: ICA TriNova, LLC, Newnan, GA (US)

( * ) Notice: Subject to any disclaimer, the term of this patent is extended or adjusted under 35 U.S.C. 154(b) by 363 days.

(21) Appl. No.: 17/949,640

(22) Filed: Sep. 21, 2022

(65) Prior Publication Data

US 2023/0089864 A1    Mar. 23, 2023

Related U.S. Application Data

(60) Provisional application No. 63/246,876, filed on Sep. 22, 2021.

(51) Int. Cl.
*A61L 9/12* (2006.01)
*A61L 9/04* (2006.01)
(Continued)

(52) U.S. Cl.
CPC ............... *A61L 9/12* (2013.01); *A61L 9/046* (2013.01); *B01D 53/44* (2013.01); *B01D 53/76* (2013.01); *B01F 23/10* (2022.01); *B01F 25/43171* (2022.01); *B01F 25/431973* (2022.01); *B01F 25/435* (2022.01); *F15D 1/06* (2013.01); *A61L 2101/06* (2020.08); *B01D 2258/06* (2013.01); *B01F 2101/2204* (2022.01)

(58) Field of Classification Search
None
See application file for complete search history.

(56) References Cited

U.S. PATENT DOCUMENTS

| 1,756,909 A | 4/1930 | Cram |
| 2,537,119 A | 1/1951 | Bauerlein |
| (Continued) | | |

FOREIGN PATENT DOCUMENTS

| KR | 102057650 B1 * | 12/2017 |
| KR | 102057650 | 12/2019 |

OTHER PUBLICATIONS

Sung et al. KR102057650B1—translated document (Year: 2019).*

(Continued)

*Primary Examiner* — Jelitza M Perez
(74) *Attorney, Agent, or Firm* — Meunier Carlin & Curfman LLC

(57) ABSTRACT

Various implementations include a fluid treatment device. The device includes an outer tube, an inner tube, a plurality of blades, and a media. The outer tube includes an inner surface. The inner tube is coaxially disposed within the outer tube. An outer surface of the inner tube and the inner surface of the outer tube define an annulus that axially extends between the ends of the inner tube. The plurality of blades is disposed within the annulus. The plurality of blades is configured to alter a component of a flow direction of fluid flowing over the blades in a circumferential direction and/or a radial direction. The media is disposed within the inner tube. The inner tube defines a plurality of perforations extending between its outer surface and inner surface. The annulus defines an entire flow path of fluid flowing between the outer tube and the inner tube.

22 Claims, 5 Drawing Sheets

(51) Int. Cl.
    *B01D 53/44*    (2006.01)
    *B01D 53/76*    (2006.01)
    *B01F 23/10*    (2022.01)
    *B01F 25/431*    (2022.01)
    *B01F 25/435*    (2022.01)
    *F15D 1/06*    (2006.01)
    *A61L 101/06*    (2006.01)
    *B01F 101/00*    (2022.01)

(56) References Cited

U.S. PATENT DOCUMENTS

| | | |
|---|---|---|
| 2,784,948 A | 3/1957 | Pahl |
| 3,190,618 A | 6/1965 | Katzen |
| 3,875,060 A | 4/1975 | Noma |
| 4,445,781 A | 5/1984 | Arena |
| 5,567,405 A | 10/1996 | Klatte et al. |
| 5,573,743 A | 11/1996 | Klatte et al. |
| 5,730,948 A | 3/1998 | Klatte et al. |
| 5,776,850 A | 7/1998 | Klatte et al. |
| 5,853,689 A | 12/1998 | Klatte |
| 5,885,543 A | 3/1999 | Klatte |
| 6,174,508 B1 | 1/2001 | Klatte |
| 6,379,643 B1 | 4/2002 | Klatte |
| 6,423,289 B1 | 7/2002 | Klatte |
| 7,347,994 B2 | 3/2008 | Tenney et al. |
| 7,922,992 B2 | 4/2011 | Ernst et al. |
| 8,709,396 B2 | 4/2014 | Tenney et al. |
| 9,382,116 B2 | 7/2016 | Isaac et al. |
| 2007/0205523 A1* | 9/2007 | Kojima ............... B01J 19/30 261/79.2 |
| 2014/0193522 A1* | 7/2014 | Isaac ............... C01B 11/022 424/661 |
| 2015/0233228 A1 | 8/2015 | Roth et al. |

OTHER PUBLICATIONS

Sung et al. KR10205765081—translated document (Year: 2019).*
International Search Report and Written Opinion in connection to PCT/US22/44123, dated Dec. 28, 2022.

* cited by examiner

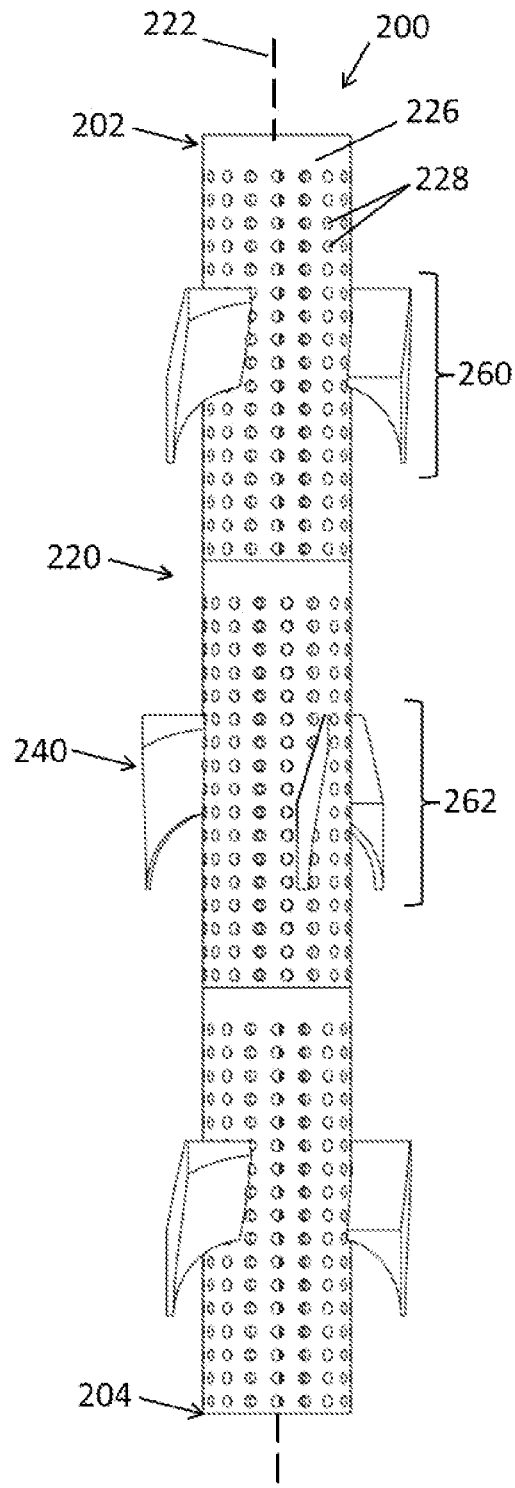
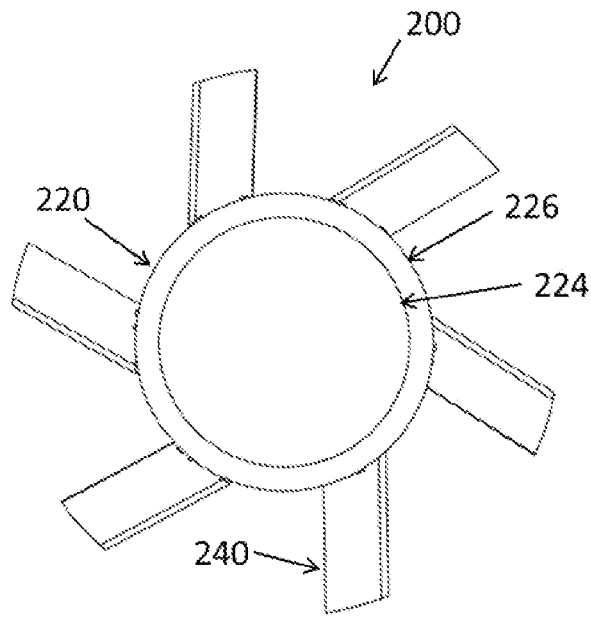
FIG. 2C
FIG. 2D

COAXIAL TUBULAR FLUID TREATMENT DEVICE AND SYSTEM

BACKGROUND

There is a need in the art for devices and methods for treating fluids, for example to reduce or eliminate contaminants such as volatile organic compounds (VOCs) and/or microorganisms in the fluids. The devices, systems, and methods disclosed herein address these and other needs.

SUMMARY OF THE DISCLOSURE

In accordance with the purposes of the disclosed devices, systems, and methods, as embodied and broadly described herein, the disclosed subject matter relates to coaxial tubular fluid treatment devices and systems, and methods of use thereof.

Disclosed herein are fluid treatment devices, the devices comprising: an outer tube comprising an inner surface; an inner tube coaxially disposed within the outer tube, the inner tube comprising an inner surface and an outer surface that extend between opposite ends of the inner tube, the outer surface of the inner tube and the inner surface of the outer tube defining an annulus that axially extends between the ends of the inner tube; a plurality of blades disposed within the annulus, the plurality of blades configured to alter a component of a flow direction of a fluid flowing over the blades in a circumferential direction and/or a radial direction; and a media disposed within the inner tube; wherein the inner tube defines a plurality of perforations extending between the outer surface and the inner surface, and wherein the annulus defines an entire flow path of the fluid flowing between the outer tube and the inner tube.

In some examples, each of the plurality of blades are fixedly coupled to the outer surface of the inner tube. In some examples, each blade having a proximal end coupled to the outer surface of the inner tube, a distal end opposite and spaced apart from the proximal end along a transverse axis of the blade, a leading edge, and a trailing edge, wherein the leading edge and trailing edge extend between the proximal and distal ends, and a longitudinal axis of the blade extends through the leading edge and the trailing edge.

In some examples, a blade plane of each blade includes the transverse axis and the longitudinal axis of the respective blade, a first subset of blades are arranged in a first row circumferentially around the inner tube, and second subset of blades are arranged in a second row circumferentially around the inner tube, wherein the first row is axially spaced apart from the second row, and the blade planes for a first blade in the first subset and a first blade in the second subset are coplanar.

In some examples, a blade plane of each blade includes the transverse axis and the longitudinal axis of the respective blade, a first subset of blades are arranged in a first row circumferentially around the inner tube and a second subset of blades are arranged in a second row circumferentially around the inner tube, wherein the first row is axially spaced apart from the second row, and the blade planes for the blades in the first row and the second row are circumferentially spaced apart.

In some examples, a plane that includes the leading edge of the first subset of blades is perpendicular to a central longitudinal axis of the inner tube. In some examples, the trailing edge of each blade is arcuate shaped, the leading edge of each blade is planar, a length of the proximal end is less than a length of the distal end, and a cross-sectional shape of each blade as taken through a plane that includes the longitudinal axis of the blade is triangular. In some examples, the transverse axis of at least one of the plurality of blades is radially spaced apart from a central longitudinal axis of the inner tube. In some examples, a surface of each blade that extends between the leading edge and the trailing edge is planar as viewed from the distal end of the blade.

In some examples, the media releases the gas into the flow path of the fluid, and wherein the flow of the fluid flowing over the blades increases the amount of the gas the media releases.

In some examples, each of the plurality of perforations are circular shaped as viewed from the outer surface of the inner tube, each of the plurality of perforations are circular shaped as viewed from the outer surface of the inner tube, the dry particles comprising the precursor have a first average particle size, each of the plurality of perforations has a perforation diameter, and the first average particle size is greater than the perforation diameter such that the media does not leak out of the plurality of perforations. In some examples, each of the plurality of perforations are circular shaped as viewed from the outer surface of the inner tube, the dry particles comprising the precursor have a first average particle size, the dry particles comprising the proton generating species have a second average particle size, each of the plurality of perforations has a perforation diameter, and the first average particle size and the second average particle size are greater than the perforation diameter such that the media does not leak out of the plurality of perforations.

In some examples, the devices further comprise a permeable liner, the liner being disposed within the inner tube adjacent the plurality of perforations. In some examples, the media is disposed within the liner. In some examples, the liner is substantially impervious to liquid water. In some examples, the liner comprises a nonwoven or paper. In some examples, the liner comprises polyethylene or polytetrafluoroethylene. In some examples, the liner is a sachet comprising three layers of membrane material forming a two-compartment sachet to separate the dry particles of the proton-generating species from the dry particles of the precursor.

In some examples, the media is configured to produce a gas from a precursor, such that the gas is released into the flow path of the fluid. In some examples, the media comprises dry particles comprising the precursor.

In some examples, the media further comprises a proton generating species. In some examples, the media further comprises dry particles comprising the proton generating species.

In some examples, the media disposed within the inner tube comprises a mixture of the dry particles comprising the precursor and the dry particles comprising the proton generating species.

In some examples, the media disposed within the inner tube comprises a layered bed comprising alternating layers of a layer comprising the dry particles comprising the precursor and a layer of the dry particles comprising the proton generating species. In some examples, the total number of layers in the layered bed is 3 or more.

In some examples, the precursor comprises a chlorine dioxide precursor and the gas comprises chlorine dioxide ($ClO_2$); wherein the precursor comprises a carbon dioxide precursor and the gas comprises carbon dioxide ($CO_2$); or a combination thereof.

In some examples, the dry particles comprising the precursor further comprise a porous carrier selected from the group consisting of zeolite crystals, silica, pumice, diatomaceous earth, bentonite, and clay, and wherein the precursor is impregnated in the porous carrier.

In some examples, the dry particles comprising the precursor include from 1% to 100%, from 1% to 90%, or from 1% to 50% by weight of the precursor.

In some examples, the precursor comprises a carbon dioxide precursor and the carbon dioxide precursor comprises a carbon-containing compound selected from the group consisting of carbonates, bicarbonates, sesquicarbonates, and combinations thereof. In some examples, the carbon-containing compound is selected from the group consisting of sodium carbonate, sodium bicarbonate, sodium sesquicarbonate, and combinations thereof.

In some examples, the precursor comprises a chlorine dioxide precursor and the chlorine dioxide precursor comprises a chlorine dioxide-producing compound selected from the group consisting of a metal chlorite, a metal chlorate, chloric acid, hypochlorous acid, and combinations thereof. In some examples, the metal chlorite comprises sodium chlorite, barium chlorite, calcium chlorite, lithium chlorite, potassium chlorite, magnesium chlorite, or combinations thereof; or wherein the metal chlorate comprises sodium chlorate, lithium chlorate, potassium chlorate, magnesium chlorate, barium chlorate, or combinations thereof.

In some examples, the dry particles comprising the proton-generating species further comprise a porous carrier selected from the group consisting of zeolite crystals, silica, pumice, diatomaceous earth, bentonite, and clay, and wherein the proton-generating species is impregnated in the porous carrier.

In some examples, the dry particles comprising the proton-generating species include from 1% to 100%, from 1% to 90%, or from 1% to 50% by weight of the dry particles of the proton-generating species.

In some examples, the proton-generating species comprises an organic acid, an inorganic acid, a metal salt, or a combination thereof. In some examples, the proton-generating species comprises an organic acid and/or an inorganic acid selected from the group consisting of acetic acid, citric acid, hydrochloric acid, phosphoric acid, propionic acid, sulfuric acid, and combinations thereof. In some examples, the proton-generating species comprises a metal salt selected from the group consisting of ferric chloride, ferric sulfate, $CaCl_2$, $ZnSO_4$, $ZnCl_2$, $CoSO_4$, $CoCl_2$, $MnSO_4$, $MgCl_2$, $CuSO_4$, $CuCl_2$, $MgSO_4$, sodium acetate, sodium citrate, sodium sulfate, sodium bisulfate, hydrogen phosphate, disodium hydrogen phosphate, and combinations thereof.

In some examples, the media is configured to release a gas, and wherein the fluid flow created by the plurality of blades increases the gas reactivity with VOCs and/or microorganisms in the fluid.

In some examples, the plurality of blades are configured to cause turbulent flow of the fluid flowing over the blades.

In some examples, the plurality of blades are configured to create a vortex in the fluid flowing over the blades.

In some examples, the fluid comprises air. In some examples, the air has a humidity of from 20% to 90% or from 50% to 80%.

Also disclosed herein are systems comprising any of the devices disclosed herein. For example, also disclosed herein are systems for treating a fluid, the systems comprising: a plurality of fluid treatment devices, each of the devices comprising: a first end; a second end opposite the first end; an outer tube comprising an inner surface that extends from the first end to the second end; an inner tube coaxially disposed with the outer tube that extends from the first end to the second end, the inner tube comprising an inner surface and an outer surface that extend between opposite ends of the inner tube, the outer surface of the inner tube and the inner surface of the outer tube defining an annulus that axially extends between the ends of the inner tube; a plurality of blades disposed within the annulus, the plurality of blades configured to alter a component of a flow direction of a fluid flowing over the blades in a circumferential direction and/or a radial direction; and a media disposed within the inner tube; wherein the inner tube defines a plurality of perforations extending between the outer surface and the inner surface, and wherein the annulus defines an entire flow path of the fluid flowing between the outer tube and the inner tube, wherein at least one of the first ends of at least one of the devices is disposable within a second end of at least another of the devices.

In some examples, at least one of the first ends of at least one of the devices is removably disposable within a second end of at least another of the devices.

In some examples, at least one of the first ends of at least one of the devices is fixedly disposable within a second end of at least another of the devices.

In some examples, each of the plurality of blades are fixedly coupled to the outer surface of the inner tube.

In some examples, each blade having a proximal end coupled to the outer surface of the inner tube, a distal end opposite and spaced apart from the proximal end along a transverse axis of the blade, a leading edge, and a trailing edge, wherein the leading edge and trailing edge extend between the proximal and distal ends, and a longitudinal axis of the blade extends through the leading edge and the trailing edge.

In some examples, a blade plane of each blade includes the transverse axis and the longitudinal axis of the respective blade, a first subset of blades are arranged in a first row circumferentially around the inner tube, and second subset of blades are arranged in a second row circumferentially around the inner tube, wherein the first row is axially spaced apart from the second row, and the blade planes for a first blade in the first subset and a first blade in the second subset are coplanar.

In some examples, a blade plane of each blade includes the transverse axis and the longitudinal axis of the respective blade, a first subset of blades are arranged in a first row circumferentially around the inner tube and a second subset of blades are arranged in a second row circumferentially around the inner tube, wherein the first row is axially spaced apart from the second row, and the blade planes for the blades in the first row and the second row are circumferentially spaced apart.

In some examples, a plane that includes the leading edge of the first subset of blades is perpendicular to a central longitudinal axis of the inner tube.

In some examples, the trailing edge of each blade is arcuate shaped, the leading edge of each blade is planar, a length of the proximal end is less than a length of the distal end, and a cross-sectional shape of each blade as taken through a plane that includes the longitudinal axis of the blade is triangular.

In some examples, the transverse axis of at least one of the plurality of blades is radially spaced apart from a central longitudinal axis of the inner tube.

In some examples, a surface of each blade that extends between the leading edge and the trailing edge is planar as viewed from the distal end of the blade.

In some examples, the systems further comprise a permeable liner, the liner being disposed within the inner tube adjacent the plurality of perforations. In some examples, the media is disposed within the liner. In some examples, the liner is substantially impervious to liquid water. In some examples, the liner comprises a nonwoven or paper. In some examples, the liner comprises polyethylene or polytetrafluoroethylene. In some examples, the liner is a sachet comprising three layers of membrane material forming a two-compartment sachet to separate the dry particles of the proton-generating species from the dry particles of the precursor.

Also disclosed herein are methods of treating a fluid using any of the systems of devices disclosed herein. For example, also disclosed herein are methods of treating a fluid, the methods comprising: providing a media within an inner tube, the inner tube comprising at least an outer surface having a plurality of blades; and disposing the inner tube within a fluid stream such that the plurality of blades and media are in contact with the fluid stream, wherein the plurality of blades alter a component of a flow direction of fluid flowing over the blades in a circumferential direction and/or a radial direction. In some examples, the media releases a gas, and wherein the fluid flow created by the plurality of the blades increases the mixing between the gas of the media and the fluid stream.

In some examples, the methods further comprise providing an outer tube disposed coaxially around the inner tube and disposing the outer tube within the fluid stream to contain and concentrate the fluid stream.

In some examples, the method is performed at a temperature of from −25° C. to 50° C., from 0° C. to 40° C., or from 32° C. to 38° C.

Additional advantages of the disclosed devices, systems, and methods will be set forth in part in the description which follows, and in part will be obvious from the description. The advantages of the disclosed devices, systems, and methods will be realized and attained by means of the elements and combinations particularly point out in the appended claims. It is to be understood that both the foregoing general description and the following detailed description are exemplary and explanatory only and are not restrictive of the disclosed devices, systems, and methods, as claimed.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

The accompanying figures, which are incorporated in and constitute a part of this specification, illustrate several aspects of the disclosure, and together with the description, serve to explain the principles of the disclosure.

Example features and implementations are disclosed in the accompanying drawings. However, the present disclosure is not limited to the precise arrangements and instrumentalities shown.

FIG. 2C is a side view of the fluid treatment device of FIG. 2A with the outer tube removed.

FIG. 2D is an end view of the fluid treatment device of FIG. 2A.

DETAILED DESCRIPTION

Figure 1A:
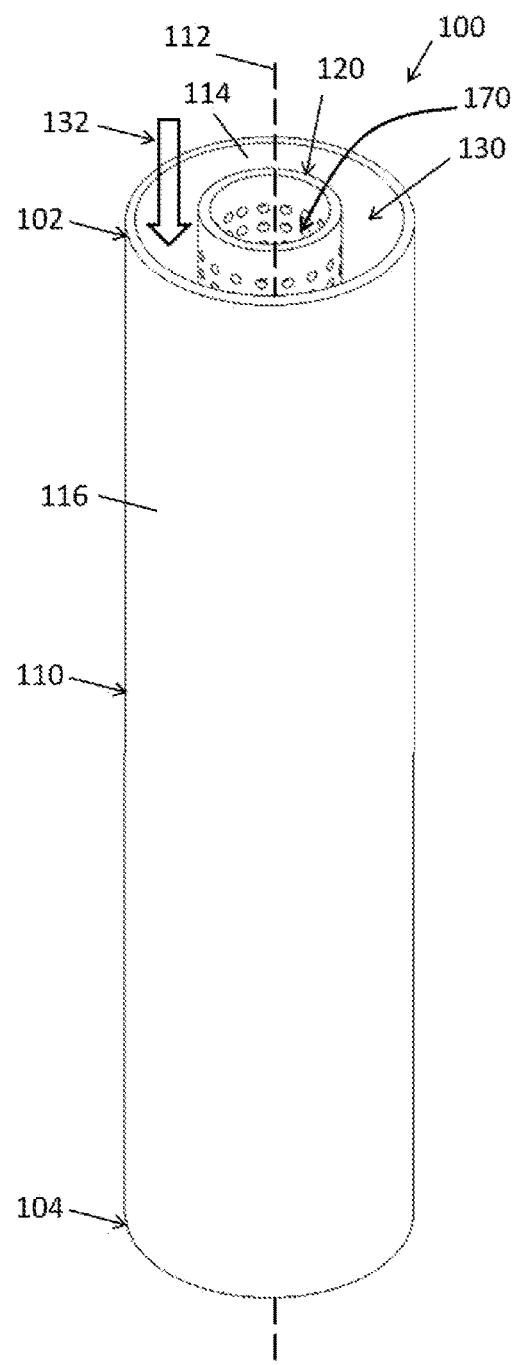
FIG. 1A is a perspective view of a fluid treatment device, according to one implementation.
Figure 1B:
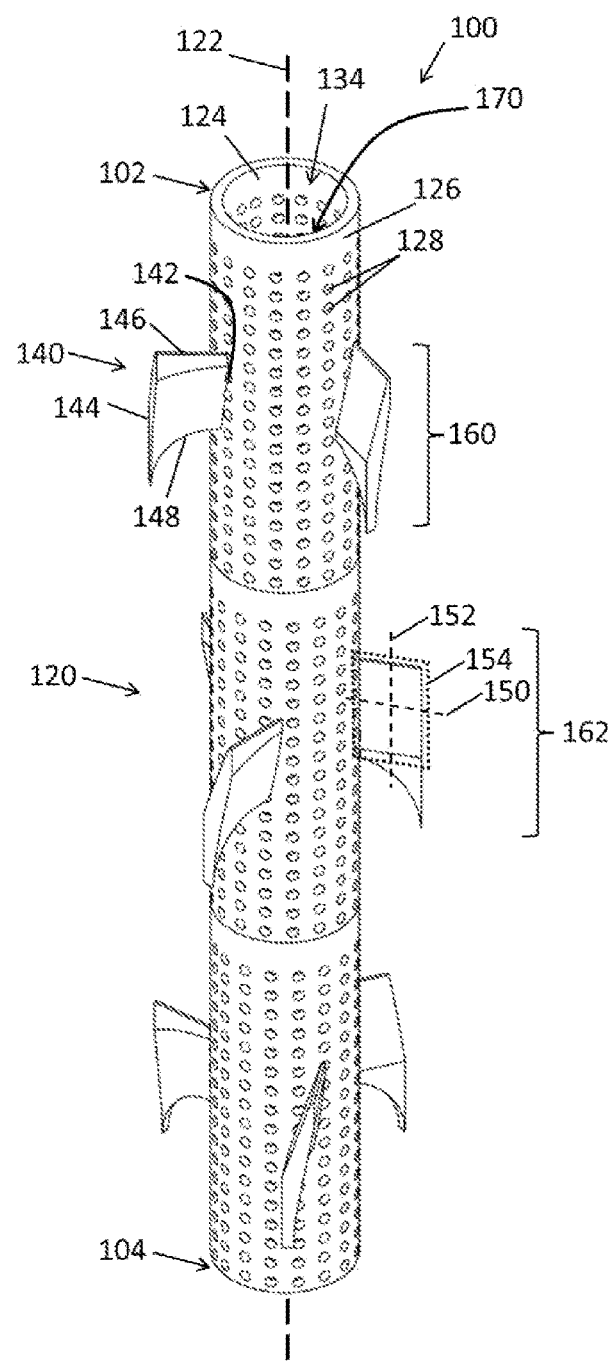
FIG. 1B is a perspective view of the fluid treatment device of FIG. 1A with the outer tube removed.
Figure 1C:
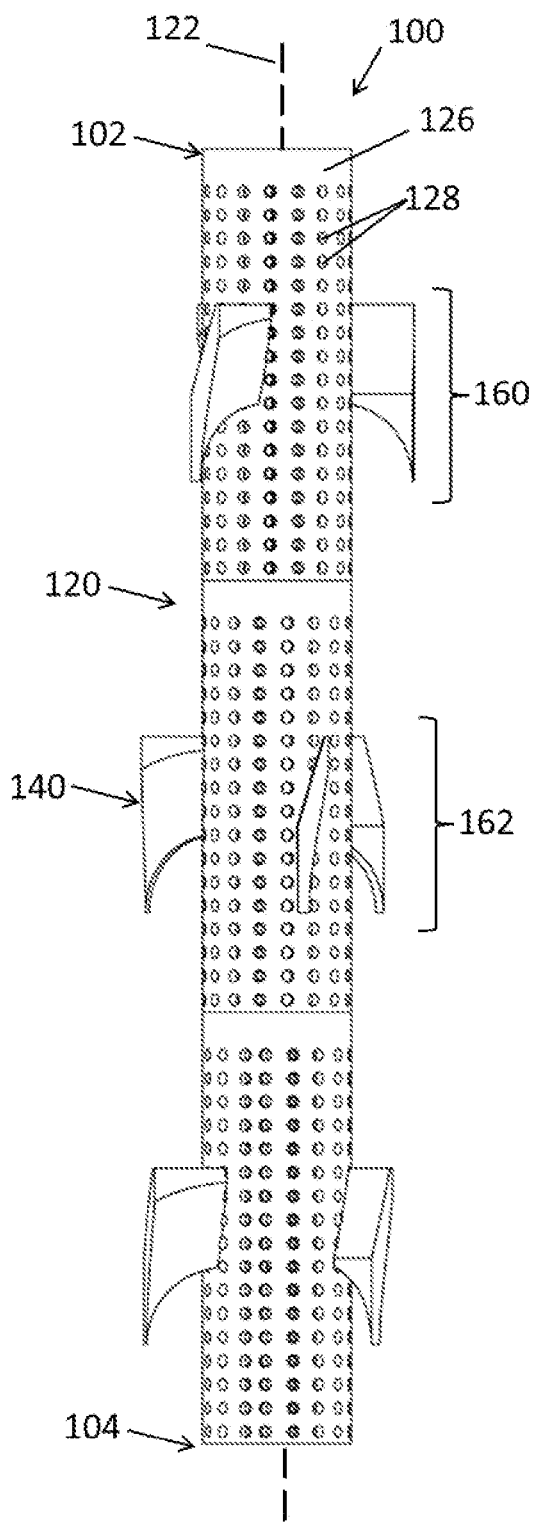
FIG. 1C is a side view of the fluid treatment device of FIG. 1A with the outer tube removed.
Figure 1D:
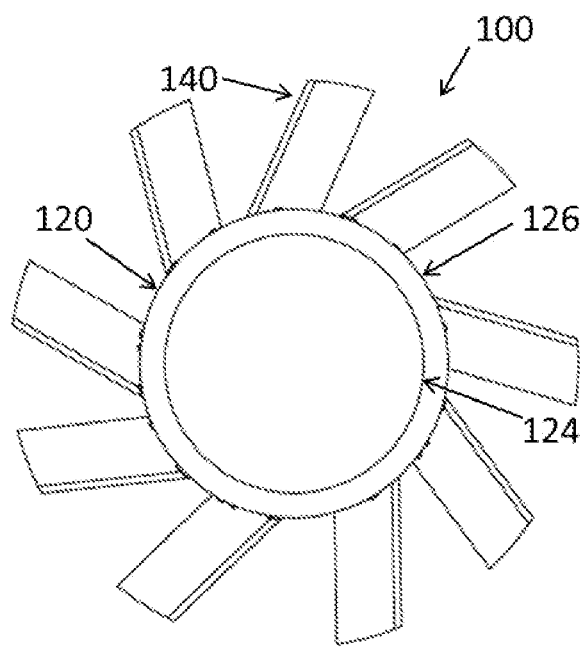
FIG. 1D is an end view of the fluid treatment device of FIG. 1A.
Figure 2A:
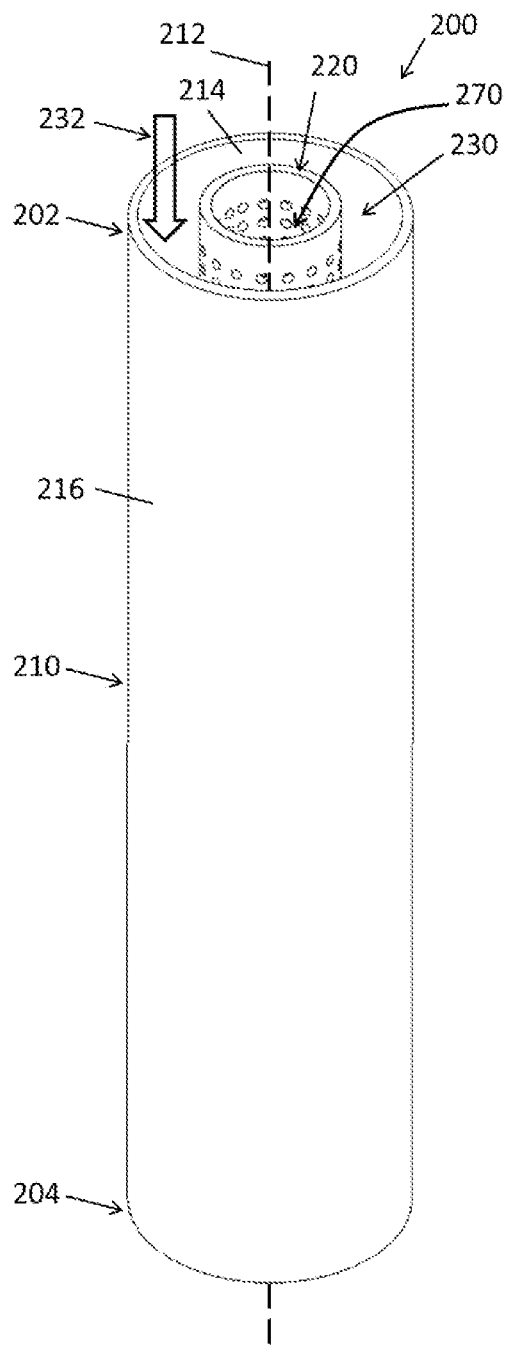
FIG. 2A is a perspective view of a fluid treatment device, according to another implementation.
Figure 2B:
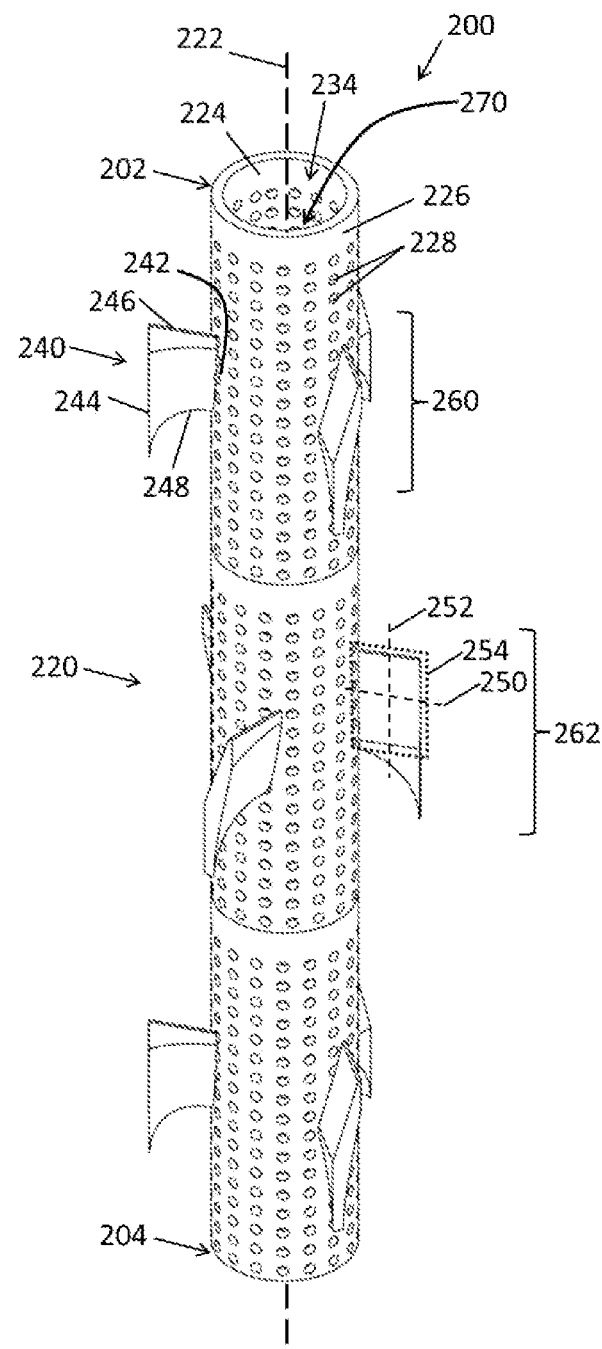
FIG. 2B is a perspective view of the fluid treatment device of FIG. 2A with the outer tube removed.

The devices, systems, and methods described herein may be understood more readily by reference to the following detailed description of specific aspects of the disclosed subject matter and the Examples included therein.

Before the present device, systems, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

In this specification and in the claims that follow, reference will be made to a number of terms, which shall be defined to have the following meanings:

The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

As used in the specification, and in the appended claims, the singular forms "a," "an," "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Exemplary" means "an example of" and is not intended to convey an indication of a preferred or ideal embodiment. "Such as" is not used in a restrictive sense, but for explanatory purposes.

It is understood that throughout this specification the identifiers "first" and "second" are used solely to aid the reader in distinguishing the various components, features, or steps of the disclosed subject matter. The identifiers "first" and "second" are not intended to imply any particular order, amount, preference, or importance to the components or steps modified by these terms.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

Disclosed herein are devices, systems, and methods that provide for treatment of a fluid.

As used herein, a "fluid" includes a liquid, a gas, a supercritical fluid, or a combination thereof. In some examples, the fluid comprises a gas, such as air, water vapor, carbon dioxide, etc. In some examples, the fluid comprises a liquid, such as liquid water.

The term "treating" or other forms of the word, such as "treat," "treated," or "treatment", as used herein refers to administration of a composition or performing a method in order to reduce, prevent, inhibit, or eliminate a particular characteristic or event (e.g., microbe growth or survival). The term "treating" or other forms of the word, such as "treat," "treated," or "treatment", as used herein includes, but is not limited to, "oxidizing," "sanitizing," "disinfecting," "sterilizing," "deodorizing," "sweetening," "acidifying," and combinations thereof. As used herein, "reduce" or other forms of the word, such as "reducing" or "reduction," refers to lowering of an event or characteristic (e.g., microbe population or activity).

The devices, systems, and methods disclosed herein providing for treatment of a fluid can comprise an inner tube disposed within an outer tube, and an annulus is defined between an outer surface of the inner tube and an inner surface of the outer tube. The inner tube defines a plurality of perforations, and a media is disposed within the inner tube such that gases produced by the media can flow out of the inner tube and into the annulus to clean the fluid as the fluid flows through the annulus. The device includes a plurality of blades disposed within the annulus to alter the flow direction of the fluid through the annulus to promote mixing of the fluid and the gas.

Various implementations include a fluid treatment device. The device includes an outer tube, an inner tube, a plurality of blades, and a media. The outer tube includes an inner surface. The inner tube is coaxially disposed within the outer tube. The inner tube includes an inner surface and an outer surface that extend between opposite ends of the inner tube. The outer surface of the inner tube and the inner surface of the outer tube defines an annulus that axially extends between the ends of the inner tube. The plurality of blades is disposed within the annulus. The plurality of blades is configured to alter a component of a flow direction of the fluid flowing over the blades in a circumferential direction and/or a radial direction. The media is disposed within the inner tube. The inner tube defines a plurality of perforations extending between the outer surface and the inner surface. The annulus defines an entire flow path of the fluid flowing between the outer tube and the inner tube.

Various other implementations include a system for treating the fluid. The system includes a plurality of fluid treatment devices as described above. Each of the devices further include a first end and a second end opposite the first end. The inner surface of the outer tube extends from the first end to the second end, and the inner tube extends from the first end to the second end. At least one of the first ends of at least one of the devices is disposable within a second end of at least another of the devices.

Various other implementations include a method of treating the fluid. The method includes providing a media within an inner tube that includes at least an outer surface having a plurality of blades and disposing the inner tube within a fluid stream such that the plurality of blades and media are in contact with the fluid stream. The plurality of blades alter a component of a flow direction of the fluid flowing over the blades in a circumferential direction and/or a radial direction.

FIGS. 1A-1D shows a fluid treatment device 100, according to one implementation. The device 100 includes a first end 102, a second end 104, an outer tube 110, an inner tube 120, a plurality of blades 140, and a media 170.

The outer tube 110 has an outer tube longitudinal axis 112, an inner surface 114, and an outer surface 116. The inner surface 114 of the outer tube 110 and the outer surface 116 of the outer tube 110 extend from the first end 102 of the device 100 to the second end 104 of the device 100.

The inner tube 120 has an inner tube longitudinal axis 122, an inner surface 124, and an outer surface 126. The inner surface 124 of the inner tube 120 and the outer surface 126 of the inner tube 120 extend from the first end 102 of the device 100 to the second end 104 of the device 100. The inner tube 120 is disposed within the outer tube 110 such that the outer tube longitudinal axis 112 is coaxial with the inner tube longitudinal axis 122. The media 170 is disposed within the inner tube 120, as discussed below.

The outer surface 126 of the inner tube 120 and the inner surface 114 of the outer tube 110 define an annulus 130 that axially extends between the first end 102 of the device 100 and the second end 104 of the device 100. The annulus 130 defines an entire flow path 132 of the fluid that flows between the inner surface 114 of the outer tube 110 in the outer surface 126 of the inner tube 120.

The outer surface 126 of the inner tube 120 defines a plurality of perforations 128 that extend from the outer surface 126 of the inner tube 120 to the inner surface 124 of the inner tube 120. The media 170 is disposed within the inner tube 120 such that the media 170 is in fluid communication with the annulus 130. The media 170 is configured to produce a gas from a precursor. The media 170 is discussed in further detail below. The plurality of perforations 128 are configured to allow the gas produced from the precursor to flow out of the inner tube 120 and into the flow path 132 of the fluid flowing through the annulus 130 defined by the outer surface 126 of the inner tube 120 and the inner surface 114 of the outer tube 110.

In some examples, the media 170 comprises dry particles comprising the precursor. The dry particles including the precursor can have a first average particle size. Each of the plurality of perforations 128 has a perforation diameter, and the first average particle size is greater than the perforation diameter such that the media 170 does not leak out of the plurality of perforations 128.

In some examples, the media 170 further comprises a proton generating species. In some examples, the media 170 further comprises dry particles comprising the proton generating species.

In some examples, the media 170 comprises dry particles comprising the precursor and dry particles comprising the proton generating species. The dry particles including the precursor have a first average particle size, and the dry particles including the proton generating species have a second average particle size. In some examples, each of the plurality of perforations 128 has a perforation diameter, and the first average particle size and the second average particle size are greater than the perforation diameter such that the media 170 does not leak out of the plurality of perforations 128. In some examples, the devices 100, 200 can include a permeable liner 134, 234 as discussed further below.

Each of the plurality of perforations 128 are circular shaped as viewed from the outer surface 126 of the inner tube 120. However, in other implementations, the plurality of perforations 128 are linear slots, ovate shaped, triangular shaped, rectangular shaped, or any other shape with a perforation dimension that is smaller than the first average particle size and/or the second average particle size such that the media 170 does not leak out of the plurality of perforations 128.

The devices 100, 200 shown in FIGS. 1A-2D can also include the permeable liner 134, 234 disposed within the inner tube 120, 220 along the inner surface 124, 224 of the inner tube 120, 220 and adjacent the plurality of perforations 128, 228. The liner 134, 234 is substantially impervious to liquid water but allows gases such as air, chlorine dioxide, and carbon dioxide to pass through. The media 170, 270 is disposed within the liner 134, 234, and the permeable liner 134, 234 aids in retaining the media 170, 270 within the inner tube 120, 220 by preventing the media 170, 270 from leaking out of the plurality of perforations 128, 228. However, in other implementations, the device does not include a permeable lining. In implementations that include a liner 134, 234, the liner prevents the media 170, 270 from leaking out of the plurality of perforations 128, 228. Thus, in implementations including a liner 134, 234, the first average particle size and the second average particle size can be smaller than the perforation diameter.

Each of the blades of the plurality of blades 140 is fixedly coupled to, and extends from, the outer surface 126 of the inner tube 120 such that the plurality of blades 140 is disposed within the annulus 130. Each of the blades 140 has a proximal end 142 coupled to the outer surface 126 of the inner tube 120, a distal end 144 opposite and space depart from the proximal end 142 along a transverse axis 150 of the blade 140, a leading edge 146 extending between the proximal end 142 and the distal end 144 of the blade 140, and a trailing edge 148 extending between the proximal end 142 and the distal end 144 of the blade 140. A blade longitudinal axis 152 extends through the leading edge 146 and the trailing edge 148 of each of the blades 140. Each of the blades 140 further includes a blade plane 154 that includes the transverse axis 150 and the blade longitudinal axis 152. The leading edge 146 of each of the blades 140 of a first subset of blades 160 is disposed in a plane that is perpendicular to the inner tube longitudinal axis 122. The transverse axis 150 of each of the blades 140 shown in FIGS. 1A-1D is radially spaced apart from the inner tube longitudinal axis 122 such that the blades 140 extend at an oblique angle to the tangent of the outer surface 126 of the inner tube 120. However, in other implementations, the transverse axis of each of the blades intersects the inner tube longitudinal axis such that the blades extend normal to the tangent of the outer surface of the inner tube.

The leading edge 146 of each blade 140 is planar, and the trailing edge 148 of each blade 140 is arcuate shaped. A surface of each blade 140 that extends between the leading edge 146 and the trailing edge 148 is planar as viewed from the distal end 144 of the blade 140. The length of the proximal end 142 is less than the length of the distal end 144. The cross-sectional shape of each blade 140, as taken through a plane that includes the blade longitudinal axis 152, is triangular.

As shown in FIGS. 2A-2D, a first subset 260 of blades 240 are arranged circumferentially around the inner tube 220 in a first row, and a second subset 262 of blades 240 are arranged circumferentially around the inner tube 220 in a second row that is axially space apart from the first row. A blade plane 254 of a first blade 240 in the first subset 260 is coplanar with a blade plane 254 of a second blade 240 in the second subset 262. However, in other implementations, such as the device shown in FIGS. 1A-1D, the blade planes 154 for the blades 140 in the first row of the first subset 160, and the blade planes 154 for the blades 140 in the second row of the second subset 162 are circumferentially spaced apart. In other implementations, the blade planes for the blades in the first row and the second row are disposed in any other arrangement relative to each other. The treatment devices 200 are similar to the device 100 shown in FIGS. 1A-1D, so similar reference numbers to those used for the device 100 shown in FIGS. 1A-1D are used to reference similar features for the devices 200 shown in FIG. 2A-2D.

For the devices 100, 200 shown in FIGS. 1A-2D, as the fluid flows axially through the anulus 130, 230 defined by the outer surface 126, 226 of the inner tube 120, 220 and the inner surface 114, 214 of the outer tube 110, 210, the plurality of blades 140, 240 alter a component of a flow direction of the fluid flowing over the blades 140, 240 in a circumferential direction and/or a radial direction. The alteration of the flow direction of the fluid promotes mixing of the gas produced by the media 170, 270 with the fluid.

The plurality of blades 140 of the device 100 shown in FIGS. 1A-1D are configured to alter the flow direction of the fluid by causing turbulent flow of the fluid flowing over the blades 140. The turbulent flow disrupts any boundary layer that may form adjacent the outer surface 126 of the inner tube 120 such that the more radially outward fluid flowing through the annulus 130 is able to move radially inwardly toward the perforations 128.

In other implementations, such as the device 200 shown in FIGS. 2A-2D, the plurality of blades 240 of the device 200 are configured to create a vortex in the fluid flowing over the blades 240. The increased swirling of the fluid flowing through the annulus 230 promotes mixing of the gas produced by the media 270 with the fluid. In other implementations, the plurality of blades of the device can be configured to cause any type of movement of the fluid flowing through the annulus to promote mixing of the gas produced by the media with the fluid.

Although each of the blades 140, 240 shown in FIGS. 1A-2D are coupled to the outer surface 126, 226 of the inner tube 120, 220, in other implementations, each of the blades are coupled to the inner surface of the outer tube. Although the blades 140, 240 shown in FIGS. 1A-2D are shaped similarly, in other implementations, each blade has any shape that alters a component of a flow direction of the fluid flowing over the blades in a circumferential direction and/or a radial direction. The blades 140, 240 of each subset of blades 160, 162, 260, 262 in FIGS. 1A-2D are equally circumferentially spaced around the inner tube 120, 220, but in other implementations, the blades are arranged in unequal circumferential spacing. In other implementations, the blades are not arranged in subsets and are disposed in any other arrangement or are disposed randomly along the outer surface of the inner tube.

In use, the media 170, 270 is disposed within the inner tube 120, 220. The media 170, 270 is configured to produce a gas from a precursor. The perforations 128, 228 defined by the inner tube 120, 220 allow the gas to flow out of the inner tube 120, 220 and into the annulus 130, 230 but are small enough to prevent the media 170, 270 from leaking through the perforations 128, 228.

A fluid stream is then caused to flow into the first end 102, 202 of the annulus 130, 230 defined by the outer surface 126, 226 of the inner tube 120, 220 and the inner surface 114, 214 of the outer tube 110, 210, through the annulus 130, 230, and out of the second end 104, 204 of the annulus 130, 230. The fluid stream can be created naturally or by a fan, a pump, or any other device capable of creating a pressure differential across the device to cause movement of fluid. The first end 102, 202 of the device 100, 200, the second end 104, 204 of the device 100, 200, or both can be coupled to a duct, tube, or other type of fluid channeling device through which the fluid stream flows such that the fluid stream is caused to flow through the annulus 130, 230 of the device 100, 200. As the fluid flows axially through the annulus 130, 230 of the device 100, 200, the plurality of blades 140, 240 alter a component of a flow direction of the fluid flowing over the blades 140, 240 in a circumferential direction and/or a radial direction, which promotes mixing of the gas produced by the media 170, 270 with the fluid.

In some examples, the fluid can comprise air. In some examples, the air can have a humidity of 20% or more, wherein the humidity is non-condensing (e.g., 25% or more, 30% or more, 35% or more, 40% or more, 45% or more, 50% or more, 60% or more, 70% or more, 80% or more, or 90% or more). In some examples, the air can have a humidity of 100% or less, wherein the humidity is non-condensing (e.g., 95% or less, 90% or less, 85% or less, 80% or less, 75% or less, 70% or less, 60% or less, 50% or less, 40% or less, or 30% or less). The amount of humidity in the air can range from any of the minimum values described above to any of the maximum values described above. For example, the air can have a humidity of from 20% to 100%, wherein the humidity is non-condensing (e.g., from 20% to 60%, from 60% to 100%, from 20% to 40%, from 40% to 60%, from 60% to 80%, from 80% to 100%, or from 50% to 80%).

In some examples, contacting or mixing the fluid with the gas produced by the media can treat the fluid, for example by adding or enriching the fluid with carbonic acid. In certain examples, treating the fluid can comprise sweetening and/or acidifying the fluid, for example with carbonic acid.

In some examples, contacting or mixing the fluid with the gas produced by the media can treat the fluid, for example by reducing or eliminating contaminants such as volatile organic compounds (VOCs) and/or microorganisms in the fluid. For example, the fluid flowing out of the second end of the annulus is treated relative to the fluid before it entered the device.

In some examples, treating the fluid can result in a reduction or deactivation in the population of microorganisms (e.g., microbes) in the fluid. In some examples, treating the fluid can result in complete (100%) reduction or deactivation in the population of microbes (e.g., elimination of the microbes).

In some examples, treating the fluid can result in a reduction of the activity (e.g., contagiousness, infectivity, transmissibility, or a combination thereof) of a population of microbes in the fluid. For example, treating the fluid can deactivate the microbes and/or reduce the contagiousness of the microbes.

In some examples, the microbes are one or more microorganisms selected from the group consisting of bacteria, viruses, fungi, and combinations thereof.

Examples of microbes include, but are not limited to adenoviruses, astrovirus, *bacillus* bacteria, *blastomyces* dermatitides, bovine coronavirus, bovine viral diarrhea, *Brucella melitensis, clostridium* bacteria, *coccidioides* immitits, common cold (e.g., rhinoviruses such as rhinovirus A, rhinovirus B, and rhinovirus C), *Corynebacterium bovis, Cryptococcus neoformans*, echovirus, enteroviruses, *Enterobacter aerogenes, Escherichia coli*, feline calicivirus (FCV), flu virus (e.g., hepatitis A, hepatitis B, herpes simplex viruses (e.g., herpes simplex 1, herpes simplex 2), *Histoplasma capsulatum*, Human Immunodeficiency Virus (HIV), influenza viruses such as influenza A, influenza virus B, and influenza virus C), *Klebsiella pneumoniae, Klebsiella oxytoca, Legionella pneumophila*, other *Legionella* species, *Mycobacterium tuberculosis, Mycoplasma* spp., norovirus, *Pasteurella* spp., poliovirus (e.g., polio virus type 1), *Proteus* spp., *Pseudomonas aeruginosa*, respiratory syncytial virus (RSV), rotavirus, *salmonella* typhosa, *Serratia marcescens, Staphylococcus aureus, Staphylococcus epidermidis, Streptococcus agalactiae, Streptococcus pyogenes, Streptococcus uberis, Trueperella pyogenes*, and vaccinia virus.

In some examples, the virus can comprise an influenza virus, a coronavirus, or a combination thereof. Examples of influenza viruses include, but are not limited to, Influenzavirus A (including the H1N1, H2N2, H3N2, H5N1, H7N7, H1N2, H9N2, H7N2, H7N3, H10N7, H7N9, and H6N1 serotypes), Influenzavirus B, Influenzavirus C, and Influenzavirus D. Examples of coronaviruses include, but are not limited to, avian coronavirus (IBV), porcine epidemic diarrhea virus (PEDV), porcine respiratory coronavirus (PRCV), transmissible gastroenteritis virus (TGEV), feline coronavirus (FCoV), feline infectious peritonitis virus (FIPV), feline enteric coronavirus (FECV), canine coronavirus (CCoV), rabbit coronavirus (RaCoV), mouse hepatitis virus (MHV), rat coronavirus (RCoV), sialodacryadenitis virus of rats (SDAV), bovine coronavirus (BCoV), bovine enterovirus (BEV), porcine coronavirus HKU15 (PorCoV HKU15), Porcine epidemic diarrhea virus (PEDV), porcine hemagglutinating encephalomyelitis virus (HEV), turkey bluecomb coronavirus (TCoV), human coronavirus (HCoV)-229E, HCoV-OC43, HCoV-HKU1, HCoV-NL63, Severe Acute Respiratory Syndrome (SARS)-Coronavirus (CoV)(SARS-CoV), Severe Acute Respiratory Syndrome (SARS)-Coronavirus (CoV)-2 (SARS-CoV-2), and middle east respiratory syndrome (MERS) coronavirus (CoV) (MERS-CoV). In some examples, the virus can comprise Severe Acute Respiratory Syndrome (SARS)-Coronavirus (CoV)-2 (SARS-CoV-2).

In some examples, treating the fluid can result in a reduction in the amount or concentration of volatile organic compounds (e.g., VOCs) in the fluid. In some examples, treating the fluid can result in complete (100%) reduction in the amount of VOCs (e.g., elimination of the VOCs).

Examples of VOCs include, but are not limited to, acetone, ethanol, isopropanol, butanal, propane, butane, hexanal, methylene chloride, benzene, perchloroethylene, ethylene glycol, formaldehyde, tetrachloroethylene, carbon tetrachloride, toluene, xylene, 1,3-butadiene, vinyl chloride, carbon disulfide, chloroform, gasoline, methyl mercaptan, hexane, $NO_x$ (e.g., NO, $NO_2$, etc.), $SO_x$ (e.g., SO, $SO_2$, $SO_3$, etc.), $H_2S$, hydrogen cyanide, hydrogen sulfide, hydrochloric acid, hydrogen fluoride, hydrogen iodide, hydrogen bromide, nitric acid vapor, chlorine, carbon disulfide, mercaptans, skunkerine, putrescine, cadaverine, trimethylamine, skatole, ethanethiol, s-ethyl thioacetate, diethyl sulfide, dimethyl sulfide, methanethiol, indole, pyridine, ammonia, methionine, derivatives thereof, and combinations thereof.

In some examples, the method can be performed at a temperature of −25° C. or more (e.g., −20° C. or more, −19° C. or more, −18° C. or more, −17° C. or more, −16° C. or more, −15° C. or more, −10° C. or more, −5° C. or more, 0° C. or more, 5° C. or more, 10° C. or more, 15° C. or more, 20° C. or more, 25° C. or more, 30° C. or more, 31° C. or more, 32° C. or more, 33° C. or more, 34° C. or more, 35° C. or more, 36° C. or more, 37° C. or more, 38° C. or more, 39° C. or more, or 40° C. or more). In some examples, the method can be performed at a temperature of 50° C. or less (e.g., 45° C. or less, 40° C. or less, 39° C. or less, 38° C. or less, 37° C. or less, 36° C. or less, 35° C. or less, 34° C. or less, 33° C. or less, 32° C. or less, 31° C. or less, 30° C. or less, 25° C. or less, 20° C. or less, 15° C. or less, 10° C. or less, 5° C. or less, 0° C. or less, −5° C. or less, −10° C. or less, −15° C. or less, −16° C. or less, or −17° C. or less). The temperature at which the method is performed can range from any of the minimum values described above to any of the maximum values described above. For example, the method can be performed at a temperature of from −25° C. to 50° C. (e.g., from −25° C. to 15° C., from 15° C. to 50° C., from −25° C. to −15° C., from −15° C. to 0° C., from 0° C. to 25° C., from 25° C. to 50° C., from 0° C. to 40° C., or from 32° C. to 38° C.).

Figure 3:
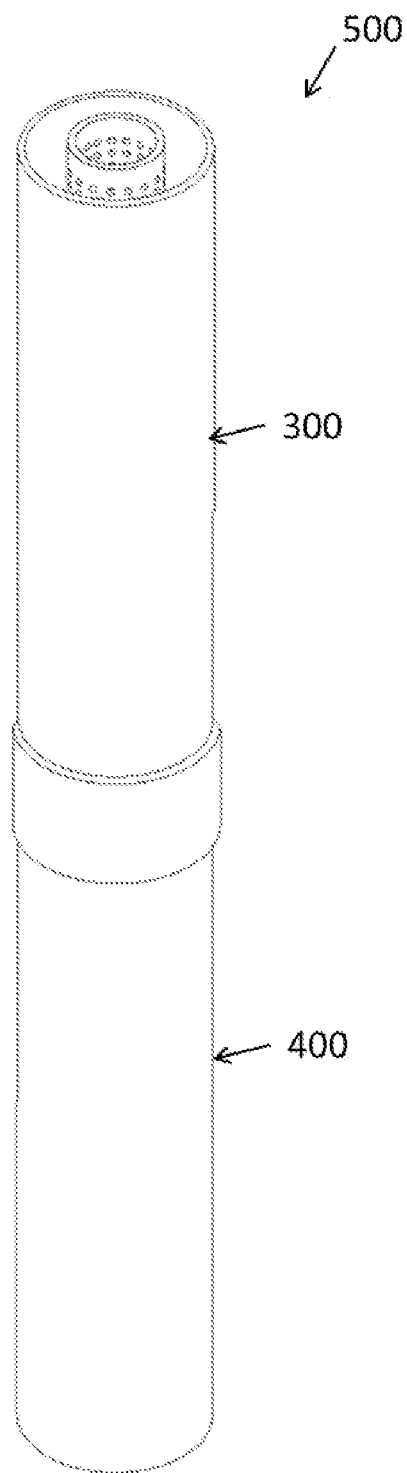
FIG. 3 is a side view of a system for treating the fluid including two fluid treatment devices coupled to each other.

In some implementations, two or more fluid treatment devices, such as those shown in FIGS. 1A-2D, can be coupled together in a modular and/or permanent system to cause fluid to pass through the two or more devices. FIG. 3 shows such a system 500 for treating a fluid that includes a first fluid treatment device 300 and a second fluid treatment device 400. The first and second treatment devices 300, 400 are similar to the device 100 shown in FIGS. 1A-1D, so similar reference numbers to those used for the device 100 shown in FIGS. 1A-1D are used to reference similar features for the devices 300, 400 shown in FIG. 3. The inner diameter of the first end 302 of the outer tube 310 of the first device 300 and the outer diameter of the second end 404 of the outer tube 410 of the second device 400 are sized such that the first end 302 of the outer tube 310 of the first device 300 is disposable within the second end 404 of the outer tube 410 of the second device 400. Thus, the first device 300 and second device 400 are couplable together such that the annulus 330 of the first device 300 and the annulus 430 of the second device 400 are axially aligned and in fluid communication with each other. Although the first end 302 of the outer tube 310 of the first device 300 is removably disposable within the second end 404 of the outer tube 410 of the second device 400 in the system 500 shown in FIG. 3, in other implementations, the first end of the outer tube of the first device is fixedly disposable within the second end of the outer tube of the second device.

The devices, systems, and methods disclosed herein providing for treatment of fluid can comprise media, wherein the media is configured to produce a gas from a precursor, such that the gas is released into the flow path of the fluid.

The precursor can be provided in any form that allows the precursor to react with protons (e.g., from a proton-generating species) to produce the gas. In some examples, the media comprises the precursor and the precursor reacts with protons in the fluid.

In some examples, the media comprises dry particles comprising the precursor. As used herein, the term "dry particles" indicates the particles have a water content of 20% or less (e.g., 15% or less, 10% or less, 5% or less, 4% or less, 3% or less, 2% or less, or 1% or less) by weight.

In some examples, the dry particles comprising the precursor are in the form of a powder. In some examples, the dry particles comprising the precursor can include a porous carrier wherein the precursor is impregnated in the porous carrier. In some examples, the porous carrier is inert. In some examples, the porous carrier has pores, channels, or the like located therein. Exemplary porous carriers include, but are not limited to, silica, pumice, diatomaceous earth, bentonite, clay, porous polymer, alumina, zeolite (e.g., zeolite crystals), or mixtures thereof.

The porous carrier can have an average particle size. "Average particle size" and "mean particle size" are used interchangeably herein, and generally refer to the statistical mean particle size of the particles in a population of particles. For example, the average particle size for a plurality of particles with a substantially spherical shape can comprise the average diameter of the plurality of particles. For an anisotropic particle, the average particle size can refer to, for example, the average maximum dimension of the particle (e.g., the length of a rod shaped particle, the diagonal of a cube shape particle, the bisector of a triangular shaped particle, etc.) Mean particle size can be measured using methods known in the art, such as sieving or microscopy.

In some examples, the porous carrier can have an average particle size, in their largest dimension, of 0.5 micrometers (microns, µm) or more (e.g., 1 µm or more, 2 µm or more, 3 µm or more, 4 µm or more, 5 µm or more, 10 µm or more, 15 µm or more, 20 µm or more, 25 µm or more, 30 µm or more, 35 µm or more, 40 µm or more, 50 µm or more, 60 µm or more, 70 µm or more, 80 µm or more, 90 µm or more, 100 µm or more, 125 µm or more, 150 µm or more, 175 µm or more, 200 µm or more, 225 µm or more, 250 µm or more, 300 µm or more, 350 µm or more, 400 µm or more, 450 µm or more, 500 µm or more, 600 µm or more, 700 µm or more, 800 µm or more, 900 µm or more, 1 millimeters (mm) or more, 2 mm or more, 3 mm or more, 4 mm or more, 5 mm or more, 6 mm or more, 7 mm or more, 8 mm or more, 9 mm or more, 10 mm or more, 15 mm or more, or 20 mm or more). In some examples, the porous carrier can have an average particle size of 25.4 mm (e.g., 1 inch) or less (e.g., 24 mm or less, 23 mm or less, 22 mm or less, 21 mm or less, 20 mm or less, 19 mm or less, 18 mm or less, 17 mm or less, 16 mm or less, 15 mm or less, 14 mm or less, 13 mm or less, 12 mm or less, 11 mm or less, 10 mm or less, 9 mm or less, 8 mm or less, 7 mm or less, 6 mm or less, 5 mm or less, 4 mm or less, 3 mm or less, 2 mm or less, 1 mm or less, 900 µm or less, 800 µm or less, 700 µm or less, 600 µm or less, 500 µm or less, 450 µm or less, 400 µm or less, 350 µm or less, 300 µm or less, 250 µm or less, 225 µm or less, 200 µm or less, 175 µm or less, 150 µm or less, 125 µm or less, 100 µm or less, 90 µm or less, 80 µm or less, 70 µm or less, 60 µm or less, 50 µm or less, 40 µm or less, 35 µm or less, 30 µm or less, 25 µm or less, 20 µm or less, 15 µm or less, 10 µm or less, or 5 µm or less). The average particle size of the porous carrier in their largest dimension can range from any of the minimum values described above to any of the maximum values described above. For example, the porous carrier can have an average particle size of from 0.5 µm to 25.4 mm (e.g., 0.5 µm to 1 mm, from 1 mm to 25.4 mm, from 0.5 µm to 100 µm, from 100 µm to 500 µm, from 500 µm to 1 mm, from 1 mm to 10 mm, from 10 mm to 25.4 mm, from 175 µm to 400 µm, or from 600 µm to 2 mm). The average particle size of the porous carrier can be selected in view of a variety of factors. In some examples, the average particle size of the porous carrier can be selected based on the presence or absence of a liner, the diameter of each of the plurality of perforations, or a combination thereof. In some embodiments, the porous carrier is uniformly impregnated throughout the volume of the porous carrier via the pores, channels, and the like, with the precursor.

In some examples, the dry particles comprising the precursor include 1% or more by weight of the precursor (e.g., 5% or more, 10% or more, 15% or more, 20% or more, 25% or more, 30% or more, 35% or more, 40% or more, 45% or more, 50% or more, 60% or more, 70% or more, 80% or more, or 90% or more). In some examples. The dry particle comprising the precursor includes 100% or less by weight of the precursor (e.g., 95% or less, 90% or less, 85% or less, 80% or less, 75% or less, 70% or less, 65% or less, 60% or less, 55% or less, 50% or less, 40% or less, 30% or less, 20% or less, or 10% or less). In some embodiments, the dry particles comprising the precursor includes a porous carrier impregnated with a precursor and the porous carrier includes 1% or more by weight of the precursor (such as in the amounts provided above) and/or 50% or less by weight of the precursor (e.g., 40% or less, 30% or less, 20% or less, or 10% or less). The amount of precursor in the dry particles comprising the precursor can range from any of the minimum values described above to any of the maximum values described above. For example, the dry particle comprising the precursor can include from 1% to 100% by weight of the precursor (e.g., from 1% to 50%, from 50% to 100%, from 1% to 25%, from 25% to 50%, from 50% to 75%, from 75% to 100%, from 1% to 90%, from 5% to 50%, from 5% to 45%, or from 10% to 40%).

In some examples, the porous carrier is impregnated with the precursor by using a porous carrier that has a low moisture (e.g., water) content. In some examples, the low moisture content is 5% or less (e.g., 4% or less, 3% or less, 2% or less, or 1% or less) by weight. In some examples, the porous carrier has an initial moisture content above 5% and thus can be dehydrated to produce a moisture content of 5% or less. In some examples, the dehydrated porous carrier is then immersed in or sprayed with an aqueous solution of the precursor at an elevated temperature (e.g., in the range from 120° F. to 190° F.) and the resulting slurry is thoroughly mixed. In some examples, the mixed slurry is then air-dried to a moisture level of 20% or less (e.g., from 0% to 20%, from 0% to 15%, from 0.25% to 10%, from 0.5% to 5%, from 0.5% to 3%) by weight to produce the impregnate (i.e., precursor impregnated in a porous carrier) disclosed herein. In some examples, the impregnate disclosed herein can be prepared without a drying step by calculating the amount of the aqueous solution of the precursor needed to achieve the desired final moisture level (e.g., from 0% to 20%, from 0% to 15%, from 0.25% to 10%, from 0.5% to 5%, from 0.5% to 3%) and adding this amount of the aqueous solution to the dehydrated porous carrier to impregnate the porous carrier, thereby forming the dry particles comprising the precursor.

In some examples, the precursor is impregnated into a porous carrier and treated with a base. In some examples, the base is any suitable base that can reduce the available protons and inhibit the reaction until the proton-generating species overcomes the base and reacts with the precursor, to enhance shelf stability and slow the reaction rate once the mixture is activated. Exemplary bases include, but are not limited to, potassium hydroxide, sodium hydroxide, calcium hydroxide, or a blend thereof.

In some embodiments, the precursor can, for example, comprise a chlorine dioxide precursor and the gas can comprise chlorine dioxide; the precursor can comprise a carbon dioxide precursor and the gas can comprise carbon dioxide; or a combination thereof.

In some examples, the precursor comprises a chlorine dioxide precursor. The chlorine dioxide precursor can be selected from any composition capable of reacting with protons to produce chlorine dioxide gas. The chlorine dioxide precursor can, for example, comprise a chlorine dioxide-producing compound selected from the group consisting of a metal chlorite, a metal chlorate, chloric acid, hypochlorous acid, and combinations thereof. Examples of metal chlorites include, but are not limited to, sodium chlorite, barium chlorite, calcium chlorite, lithium chlorite, potassium chlorite, magnesium chlorite, and combinations thereof. Examples of metal chlorates include, but are not limited to, sodium chlorate, lithium chlorate, potassium chlorate, magnesium chlorate, barium chlorate, and combinations thereof. In some examples, the chlorine dioxide precursor is impregnated in a porous carrier such as zeolite crystals as described above and as described in U.S. Pat. Nos. 5,567,405; 5,573,743; 5,730,948; 5,776,850; 5,853,689; 5,885,543; 6,174,508; 6,379,643; 6,423,289; 7,347,994; 7,922,992; and 9,382,116, which are incorporated by reference in their entirety.

In some examples, the precursor comprises a carbon dioxide precursor. The carbon dioxide precursor can be selected from any composition capable of reacting with protons to produce carbon dioxide gas or carbonic acid. The carbon dioxide precursor can, for example, comprise a carbon-containing compound selected from the group consisting of carbonates, bicarbonates, sesquicarbonates, and combinations thereof. Examples of carbon-containing compounds include, but are not limited to, sodium carbonate, sodium bicarbonate, sodium sesquicarbonate, and combinations thereof. In some examples, the carbon dioxide precursor is impregnated in a porous carrier such as zeolite crystals as described above and as described in U.S. Pat. Nos. 7,992,992 and 8,709,396, which are hereby incorporated herein by reference in their entirety.

The media can, for example, further comprise a proton generating species. A proton-generating species as disclosed herein can be any composition capable of generating protons to react with the precursor to generate the gas. The proton-generating species can, for example, comprise an organic acid, an inorganic acid, a metal salt, or a combination thereof.

In some examples, the organic acid and/or an inorganic acid can be selected from the group consisting of acetic acid, citric acid, hydrochloric acid, phosphoric acid, propionic acid, sulfuric acid, and combinations thereof.

In some embodiments, proton-generating species comprises a metal salt. In some embodiments, the metal salt is a chloride, sulfate, phosphate, propionate, acetate, or citrate that combines with water to produce an acid, i.e., protons. In some embodiments, the metal is an alkali metal, alkaline earth metal, or a transition metal.

Examples of metal salts include, but are not limited to, ferric chloride, ferric sulfate, $CaCl_2$, $ZnSO_4$, $ZnCl_2$, $CoSO_4$, $CoCl_2$, $MnSO_4$, $MgCl_2$, $CuSO_4$, $CuCl_2$, $MgSO_4$, sodium acetate, sodium citrate, sodium sulfate, sodium bisulfate, hydrogen phosphate, disodium hydrogen phosphate, and combinations thereof.

In some embodiments, the proton-generating species is a metal salt that can also act as a water-retaining substance (e.g., $CaCl_2$, $MgSO_4$).

In some embodiments, the proton-generating species is activated to produce protons by contacting the proton-generating species with a moisture-containing (or water-containing) fluid. In some embodiments, the metal salt is ferric chloride, ferric sulfate, or a mixture thereof, and these iron salts can absorb water in addition to functioning as a proton-generating species. In some embodiments, the moisture-containing fluid is liquid water or an aqueous solution. In some embodiments, the moisture-containing fluid is a moisture-containing gas such as air or water vapor. In some embodiments, the protons produced by the proton-generating species react with the precursor to the gas. The proton-generating species can also be activated other than by exposure to a moisture-containing fluid. In some embodiments, the proton-generating species can be activated and can release protons upon exposure to the water in the powders or impregnated porous carrier containing the precursor.

The proton-generating species can be provided in any form that allows the release of protons.

In some examples, the media further comprises dry particles comprising the proton generating species. As used herein, the term "dry particles" indicates the particles have a water content of 20% or less (e.g., 15% or less, 10% or less, 5% or less, 4% or less, 3% or less, 2% or less, or 1% or less) by weight.

In some examples, the dry particles comprising the proton-generating species are in the form of a powder. In some examples, the dry particles comprising the proton-generating species can further comprise a porous carrier and the proton-generating species can be impregnated in the porous carrier. In some examples, the porous carrier is inert. In some examples, the porous carrier has pores, channels, or the like located therein. Exemplary porous carriers include, but are not limited to, silica, pumice, diatomaceous earth, bentonite, clay, porous polymer, alumina, zeolite (e.g., zeolite crystals), or mixtures thereof.

In some examples, the porous carrier can have an average particle size, in their largest dimension, of 0.5 micrometers (microns, μm) or more (e.g., 1 μm or more, 2 μm or more, 3 μm or more, 4 μm or more, 5 μm or more, 10 μm or more, 15 μm or more, 20 μm or more, 25 μm or more, 30 μm or more, 35 μm or more, 40 μm or more, 50 μm or more, 60 μm or more, 70 μm or more, 80 μm or more, 90 μm or more, 100 μm or more, 125 μm or more, 150 μm or more, 175 μm or more, 200 μm or more, 225 μm or more, 250 μm or more, 300 μm or more, 350 μm or more, 400 μm or more, 450 μm or more, 500 μm or more, 600 μm or more, 700 μm or more, 800 μm or more, 900 μm or more, 1 millimeters (mm) or more, 2 mm or more, 3 mm or more, 4 mm or more, 5 mm or more, 6 mm or more, 7 mm or more, 8 mm or more, 9 mm or more, 10 mm or more, 15 mm or more, or 20 mm or more). In some examples, the porous carrier can have an average particle size of 25.4 mm (e.g., 1 inch) or less (e.g., 24 mm or less, 23 mm or less, 22 mm or less, 21 mm or less, 20 mm or less, 19 mm or less, 18 mm or less, 17 mm or less, 16 mm or less, 15 mm or less, 14 mm or less, 13 mm or less, 12 mm or less, 11 mm or less, 10 mm or less, 9 mm or less, 8 mm or less, 7 mm or less, 6 mm or less, 5 mm or less, 4 mm or less, 3 mm or less, 2 mm or less, 1 mm or less, 900 μm or less, 800 μm or less, 700 μm or less, 600 μm or less, 500 μm or less, 450 μm or less, 400 μm or less, 350 μm or less, 300 μm or less, 250 μm or less, 225 μm or less, 200 μm or less, 175 μm or less, 150 μm or less, 125 μm or less, 100 μm or less, 90 μm or less, 80 μm or less, 70 μm or less, 60 μm or less, 50 μm or less, 40 μm or less, 35 μm or less, 30 μm or less, 25 μm or less, 20 μm or less, 15 μm or less, 10 μm or less, or 5 μm or less)., in their largest dimension. The average particle size of the porous carrier in their largest dimension can range from any of the minimum values described above to any of the maximum values described above. For example, the porous carrier can have an average particle size of from 0.5 μm to 25.4 mm (e.g., 0.5 μm to 1 mm, from 1 mm to 25.4 mm, from 0.5 μm to 100 μm, from 100 μm to 500 μm, from 500 μm to 1 mm, from 1 mm to 10 mm, from 10 mm to 25.4 mm, from 175 μm to 400 μm, or from 600 μm to 2 mm). The average particle size of the porous carrier can be selected in view of a variety of factors.

In some examples, the average particle size of the porous carrier can be selected based on the presence or absence of a liner, the diameter of each of the plurality of perforations, or a combination thereof. In some examples, the porous carrier is uniformly impregnated throughout the volume of the porous carrier via the pores, channels, and the like, with the proton-generating species.

In some examples, the dry particles comprising the proton-generating species include 1% or more by weight of the proton-generating species (e.g., 5% or more, 10% or more, 15% or more, 20% or more, 25% or more, 30% or more, 35% or more, 40% or more, 45% or more, 50% or more, 60% or more, 70% or more, 80% or more, or 90% or more). In some examples, the dry particles comprising the proton-generating species include 100% or less by weight of the proton-generating species (e.g., 95% or less, 90% or less, 85% or less, 80% or less, 75% or less, 70% or less, 65% or less, 60% or less, 55% or less, 50% or less, 40% or less, 30% or less, 20% or less, or 10% or less). In some embodiments, the dry particles comprising the proton-generating species includes a porous carrier impregnated with a proton-generating species and the porous carrier includes 1% or more by weight of the proton-generating species (such as in the amounts provided above) and/or 50% or less by weight of the proton-generating species (e.g., 40% or less, 30% or less, 20% or less, or 10% or less). The amount of proton-generating species in the dry particles comprising the proton-generating species can range from any of the minimum values described above to any of the maximum values described above. For example, the dry particle comprising the proton-generating species can include from 1% to 100% by weight of the proton-generating species (e.g., from 1% to 50%, from 50% to 100%, from 1% to 25%, from 25% to 50%, from 50% to 75%, from 75% to 100%, from 1% to 90%, from 5% to 50%, from 5% to 45%, or from 10% to 40%). In some examples, the porous carrier impregnated with the proton-generating species is separate from the porous carrier impregnated with the precursor.

In some examples, the porous carrier is impregnated with the proton-generating species by using a porous carrier that has a low moisture (e.g., water) content. In some embodiments, the low moisture content is 5% or less (e.g., 4% or less, 3% or less, 2% or less, or 1% or less) by weight. In some embodiments, the porous carrier has an initial moisture content above 5% and thus can be dehydrated to produce a moisture content of 5% or less. In some embodiments, the dehydrated porous carrier is then immersed in or sprayed with an aqueous solution of the proton-generating species at an elevated temperature (e.g., in the range from 120° F. to 190° F.) and the resulting slurry is thoroughly mixed. In some embodiments, the mixed slurry is then air-dried to a moisture level of from 0% to 20% (e.g., from 0% to 15%, from 0.25% to 10%, from 0.5% to 5%, from 0.5% to 3%) by weight to produce an impregnate (i.e., proton-generating species impregnated in a porous carrier). In some embodiments, the impregnate disclosed herein can be prepared without a drying step by calculating the amount of the aqueous solution of the proton-generating species needed to achieve the desired final moisture level (e.g., from 0% to 15%, from 0.25% to 10%, from 0.5% to 5%, from 0.5% to 3%) and adding this amount of the aqueous solution to the dehydrated porous carrier to impregnate the porous carrier. In some embodiments, the proton-generating species is provided in excess of the stoichiometric amount required to produce the gas when reacting with the precursor.

In some examples, the media can further comprise a deliquescent. Examples of deliquescents include, but are not limited to, aluminum chloride, aluminum nitrate, ammonium bifluoride, cadmium nitrate, cesium hydroxide, calcium chloride, calcium iodide, cobalt(II) chloride, gold(III) chloride, iron(III) chloride, iron(III) nitrate, lithium iodide, lithium nitrate, magnesium chloride, magnesium iodide, manganese(II) sulfate, mesoxalic acid, potassium carbonate, potassium oxide, silver perchlorate, sodium formate, sodium nitrate, tachyhydrite, taurocholic acid, tellurium tetrachloride, tin(II) chloride, tin(II) sulfate, yttrium(III) chloride, zinc chloride, and combinations thereof. In some examples, the deliquescent is in the form of a powder. In some examples, the deliquescent can be impregnated in a porous carrier. In some examples, the porous carrier is inert. In some examples, the porous carrier has pores, channels, or the like located therein. In some examples, the porous carrier is uniformly impregnated throughout the volume of the porous carrier via the pores, channels, and the like, with the deliquescent. In some examples, the porous carrier impregnated with the deliquescent is separate from the porous carrier impregnated with the precursor and/or the porous carrier impregnated with the proton-generating species.

In some examples, the media can further comprise a desiccant. Examples of desiccants include, but are not limited to, activated alumina, benzophenone, bentonite clay, calcium oxide, calcium sulfate (Drierite), calcium sulfonate, copper(II) sulfate, lithium chloride, lithium bromide, magnesium sulfate, magnesium perchlorate, molecular sieves, potassium carbonate, potassium hydroxide, silica gel, sodium, sodium chlorate, sodium chloride, sodium hydroxide, sodium sulfate, sucrose, and combinations thereof. In some examples, the desiccant is in the form of a powder. In some examples, the desiccant can be impregnated in a porous carrier. In some examples, the porous carrier is inert. In some examples, the porous carrier has pores, channels, or the like located therein. In some examples, the porous carrier is uniformly impregnated throughout the volume of the porous carrier via the pores, channels, and the like, with the desiccant. In some examples, the porous carrier impregnated with the desiccant is separate from the porous carrier impregnated with the precursor and/or the porous carrier impregnated with the proton-generating species.

In some examples, the media comprises dry particles comprising the precursor and dry particles comprising the proton generating species.

In some examples, the media disposed within the inner tube comprises a mixture of the dry particles comprising the precursor and the dry particles comprising the proton generating species.

In some examples, the media disposed within the inner tube comprises a layered bed comprising alternating layers of a layer comprising the dry particles comprising the precursor and a layer of the dry particles comprising the proton generating species. In some examples, the total number of layers in the layered bed is 3 or more (e.g., 4 layers or more, 5 layers or more, 6 layers or more, 7 layers or more, 8 layers or more, 9 layers or more, 10 layers or more, 11 layers or more, 12 layers or more, 13 layers or more, 14 layers or more, 15 layers or more, 16 layers or more, 17 layers or more, 18 layers or more, 19 layers or more, 20 layers or more, 22 layers or more, 24 layers or more, 26 layers or more, 28 layers or more, 30 layers or more, 35 layers or more, or 40 layers or more). In some examples, the total number of layers in the layered bed is 48 layers or less (e.g., 46 layers or less, 44 layers or less, 42 layers or less, 40 layers or less, 38 layers or less, 36 layers or less, 34 layers or less, 32 layers or less, 30 layers or less, 28 layers or less, 26 layers or less, 24 layers or less, 22 layers or less, 20 layers or less, 19 layers or less, 18 layers or less, 17 layers or less, 16 layers or less, 15 layers or less, 14 layers or less, 13 layers or less, 12 layers or less, 11 layers or less, 10 layers or less, 9 layers or less, 8 layers or less, 7 layers or less, 6 layers or less, or 5 layers or less). The total number of layered in the layered bed can range from any of the minimum values described above to any of the maximum values described above. For example, the total number of layers in the layered bed can be from 3 layers to 48 layers (e.g., from 3 layers to 24 layers, from 24 layers to 48 layers, from 3 layers to 30 layers, from 3 layers to 20 layers, or from 4 layers to 16 layers).

In some examples, the bed can further include a porous woven or nonwoven layer between one or more of the layers to separate the layers. The woven or nonwoven layer can be formed of a polymer material such as polyethylene, polypropylene or polyester (e.g., polyethylene terephthalate (PET)). For example, the porous separator layer can be a spun bond nonwoven polyester layer.

In some examples, two or more fluid treatment devices can be coupled together in a modular and/or permanent system to cause fluid to pass through the two or more devices. FIG. 3 shows such a system 500 for treating a fluid that includes a first fluid treatment device 300 and a second fluid treatment device 400. In certain examples, the media disposed within the inner tube of the first fluid device can comprise the precursor (e.g., dry particles comprising the precursor) and the media disposed within the second fluid device can comprise the proton-generating species (e.g., dry particles comprising the proton-generating species), or vice-versa.

The devices, systems, and methods disclosed herein providing for treatment of fluid can comprise media, wherein the media is configured to produce a gas from a precursor, such that the gas is released into the flow path of the fluid. In some examples, the media releases the gas into the flow path of fluid, and wherein the flow of the fluid flowing over the blades increases the amount of the gas the media releases. In some examples, the media is configured to release a gas, and wherein the fluid flow created by the plurality of blades increases the gas reactivity with VOCs and/or microorganisms in the fluid.

In some embodiments, the proton-generating species is provided in the same enclosure with an impregnate comprising the precursor impregnated in a porous carrier. For example, the media can be disposed within a permeable liner disposed within the inner tube along the inner surface of the inner tube and adjacent the plurality of perforations. In some embodiments, the enclosing material (e.g., liner) can include any enclosing material that is substantially impervious to liquid water. In some embodiments, the media is placed in a humidity-activated sachet and enclosed within a liner. Exemplary liners include, but are not limited to, a nonwoven or paper. Exemplary commercially available materials for the liner include, but are not limited to, polyethylene such as TYVEK® (high density polyethylene) and polytetrafluoroethylene such as GORE-TEX®. In some embodiments, the liner allows water vapor to enter. In some embodiments, the liner allows the gas to be released therefrom into the flow path of the fluid. In some embodiments, the liner is a sachet comprising three layers of membrane material forming a two-compartment sachet to separate the proton-generating species (whether impregnated in a porous carrier or not) from the precursor (whether impregnated in a porous carrier or not). In some embodiments, the multiple layers of membrane material can be selected from different membrane materials, wherein the permeability of the outer membrane can determine how fast humidity can enter the sachet to activate the precursor and the proton-generating species. In some embodiments, the multiple layers of membrane material can be selected from different membrane materials, wherein the center membrane can determine how fast the protons from the proton-generating source can pass to the precursor to react and generate the gas.

A number of example implementations are provided herein. However, it is understood that various modifications can be made without departing from the spirit and scope of the disclosure herein.

Disclosed are materials, systems, devices, methods, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

What is claimed is:

1. A fluid treatment device, the device comprising:
an outer tube comprising an inner surface;
an inner tube coaxially disposed within the outer tube, the inner tube comprising an inner surface and an outer surface that extend between opposite ends of the inner tube, the outer surface of the inner tube and the inner surface of the outer tube defining an annulus that axially extends between the ends of the inner tube;
a plurality of blades disposed within the annulus, the plurality of blades configured to alter a component of a flow direction of a fluid flowing over the plurality of blades in a circumferential direction and/or a radial direction, wherein each blade of the plurality of blades comprises:
a proximal end coupled to the outer surface of the inner tube,
a distal end opposite and spaced apart from the proximal end along a transverse axis of the blade,
a leading edge, and
a trailing edge,
wherein the leading edge and the trailing edge extend between the proximal and distal ends, and a longitudinal axis of the blade extends through the leading edge and the trailing edge, a blade plane of each blade includes the transverse axis and the longitudinal axis of the respective blade, wherein the transverse axis of each blade is radially spaced apart from an inner tube longitudinal axis of the inner tube such that each blade of the plurality of blades extends at an oblique angle relative to a tangent of the outer surface of the inner tube; and
a media disposed within the inner tube;
wherein the inner tube defines a plurality of perforations extending between the outer surface and the inner surface,
wherein the annulus defines an entire flow path of the fluid flowing between the outer tube and the inner tube,
wherein a first subset of blades of the plurality of blades are arranged in a first row circumferentially around the inner tube, and second subset of blades of the plurality of blades are arranged in a second row circumferentially around the inner tube, wherein the first row is axially spaced apart from the second row, and the blade planes for a first blade in the first subset and a first blade in the second subset are coplanar, and
wherein the flow direction of the fluid flowing over the blades is altered such that a radially outward portion of the fluid is moved radially inwardly toward the plurality of perforations of the inner tube.

2. The device of claim 1, wherein: a cross-sectional shape of each blade as taken through a plane that includes the blade longitudinal axis is triangular.

3. The device of claim 1, wherein the media is configured to produce a gas from a precursor, such that the gas is released into the flow path of the fluid.

4. The device of claim 3, wherein the media comprises dry particles comprising the precursor.

5. The device of claim 3, wherein the media further comprises a proton generating species.

6. The device of claim 3, wherein the media disposed within the inner tube comprises a mixture of dry particles comprising the precursor and dry particles comprising a proton generating species.

7. The device of claim 3, wherein the precursor comprises a chlorine dioxide precursor and the gas comprises chlorine dioxide ($ClO_2$); wherein the precursor comprises a carbon dioxide precursor and the gas comprises carbon dioxide ($CO_2$); or a combination thereof.

8. The device of claim 4, wherein the dry particles comprising the precursor further comprise a porous carrier selected from the group consisting of zeolite crystals, silica, pumice, diatomaceous earth, bentonite, and clay, and wherein the precursor is impregnated in the porous carrier.

9. The device of claim 4, wherein the dry particles comprising the precursor include from 1% to 100% by weight of the precursor.

10. The device of claim 3, wherein the precursor comprises a chlorine dioxide precursor and the chlorine dioxide precursor comprises a chlorine dioxide-producing compound selected from the group consisting of a metal chlorite, a metal chlorate, chloric acid, hypochlorous acid, and combinations thereof.

11. The device of claim 10, wherein the metal chlorite comprises sodium chlorite, barium chlorite, calcium chlorite, lithium chlorite, potassium chlorite, magnesium chlorite, or combinations thereof; or wherein the metal chlorate comprises sodium chlorate, lithium chlorate, potassium chlorate, magnesium chlorate, barium chlorate, or combinations thereof.

12. The device of claim 5, wherein the media comprising the proton-generating species further comprise a porous carrier selected from the group consisting of zeolite crystals, silica, pumice, diatomaceous earth, bentonite, and clay, and wherein the proton-generating species is impregnated in the porous carrier.

13. The device of claim 5, wherein the media comprising the proton-generating species include from 1% to 100% by weight of the media of the proton-generating species.

14. The device of claim 5, wherein the proton-generating species comprises an organic acid, an inorganic acid, a metal salt, or a combination thereof.

15. The device of claim 14, wherein the proton-generating species comprises an organic acid and/or an inorganic acid selected from the group consisting of acetic acid, citric acid, hydrochloric acid, phosphoric acid, propionic acid, sulfuric acid, and combinations thereof.

16. The device of claim 14, wherein the proton-generating species comprises a metal salt selected from the group consisting of ferric chloride, ferric sulfate, $CaCl_2$, $ZnSO_4$, $ZnCl_2$, $CoSO_4$, $CoCl_2$, $MnSO_4$, $MgCl_2$, $CuSO_4$, $CuCl_2$, $MgSO_4$, sodium acetate, sodium citrate, sodium sulfate, sodium bisulfate, hydrogen phosphate, disodium hydrogen phosphate, and combinations thereof.

17. The device of any one of claims 6, wherein each of the plurality of perforations are circular shaped as viewed from the outer surface of the inner tube, the dry particles comprising the precursor have a first average particle size, the dry particles comprising the proton generating species have a second average particle size, each of the plurality of perforations has a perforation diameter, and the first average particle size and the second average particle size are greater than the perforation diameter such that the media does not leak out of the plurality of perforations.

18. The device of claim 1, wherein the media is configured to release a gas, and wherein the fluid flow created by the plurality of blades increases the gas reactivity with VOCs and/or microorganisms in the fluid.

19. The device of claim 1, wherein the plurality of blades are configured to cause turbulent flow of the fluid flowing over the blades.

20. The device of claim 1, wherein the plurality of blades are configured to create a vortex in the fluid flowing over the blades.

21. A system for treating a fluid, the system comprising:
a plurality of fluid treatment devices including the fluid treatment device of claim 1,
wherein at least one of the first ends of at least one of the devices is disposable within a second end of at least another of the devices.

22. A fluid treatment device, the device comprising:
an outer tube comprising an inner surface;
an inner tube coaxially disposed within the outer tube, the inner tube comprising an inner surface and an outer surface that extend between opposite ends of the inner tube, the outer surface of the inner tube and the inner surface of the outer tube defining an annulus that axially extends between the ends of the inner tube;
a plurality of blades disposed within the annulus, the plurality of blades configured to alter a component of a flow direction of a fluid flowing over the blades in a circumferential direction and/or a radial direction; and
a media disposed within the inner tube;
wherein the inner tube defines a plurality of perforations extending between the outer surface and the inner surface, and
wherein the annulus defines an entire flow path of the fluid flowing between the outer tube and the inner tube,
wherein the media disposed within the inner tube comprises a mixture of dry particles comprising a precursor and dry particles comprising a proton generating species,
wherein each of the plurality of perforations are circular shaped as viewed from the outer surface of the inner tube, the dry particles comprising the precursor have a first average particle size, the dry particles comprising the proton generating species have a second average particle size, each of the plurality of perforations has a perforation diameter, and the first average particle size and the second average particle size are greater than the perforation diameter such that the media does not leak out of the plurality of perforations.

* * * * *